United States Patent [19]

Terino

[11] Patent Number: 4,990,160
[45] Date of Patent: Feb. 5, 1991

[54] EXTENDED CHIN AND MANDIBLE IMPLANTS

[76] Inventor: Edward Terino, 28222 Agoura Rd., Ste. 241, Agoura Hills, Calif. 91301

[21] Appl. No.: 404,005

[22] Filed: Sep. 5, 1989

Related U.S. Application Data

[63] Continuation of Ser. No. 154,535, Feb. 16, 1988, abandoned, which is a continuation-in-part of Ser. No. 822,172, Jan. 24, 1986, abandoned.

[51] Int. Cl.⁵ .................................................. A61F 2/02
[52] U.S. Cl. .......................................... 623/11; 623/16
[58] Field of Search .............................. 623/11, 16, 66

[56] References Cited

U.S. PATENT DOCUMENTS 3,216,023 11/1965 Morgan .......................... 128/136 X
4,344,191 8/1982 Wagner ................................ 623/16

*Primary Examiner*—Alan W. Cannon
*Attorney, Agent, or Firm*—Richard D. Slehofer

[57] ABSTRACT

An extended implant is surgically inserted underneath the soft tissue and superposed on the human mandible. The implant has a convex anterior surface. The posterior surface has a concave surface for cooperating with the irregular bony surface of the mandible. The medial sagittal area of the convex surface has a protuberance for augmenting and providing a natually appearing chin contour when the implant is in place. The implant extends and tapers bilaterally from the protuberance. The superior edge has bilateral arcuate-shaped depressions for avoiding the mental nerves. The snug fit of the implant against the mandible prevents movement thereby precluding bone erosion below the lower teeth. The snug fit and the arcuate depressions preclude painful impingement of the mental nerves.

4 Claims, 4 Drawing Sheets

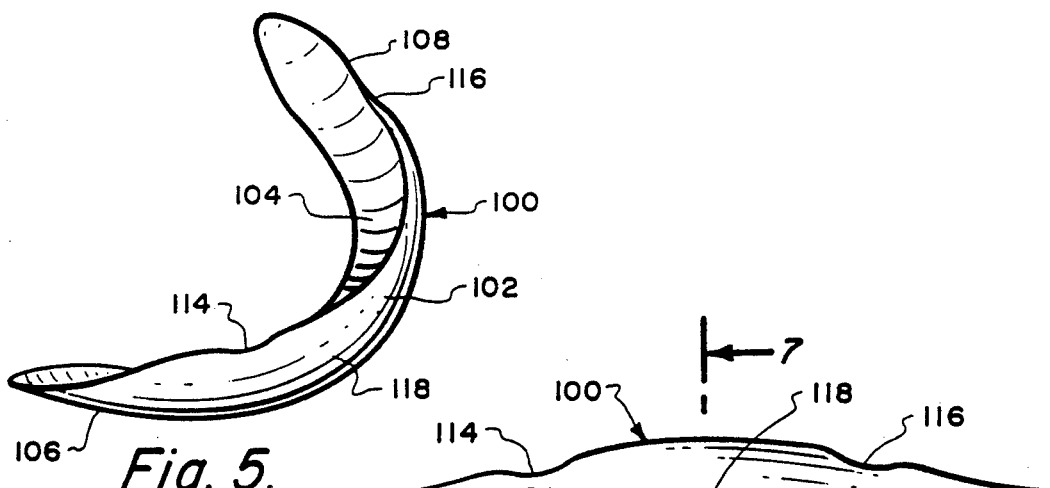
Fig. 5.
Fig. 6.
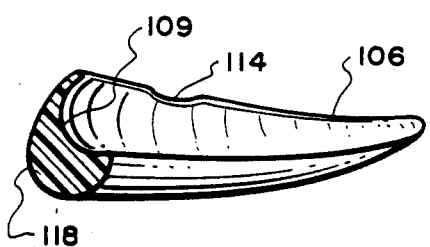
Fig. 7.
Fig. 8.
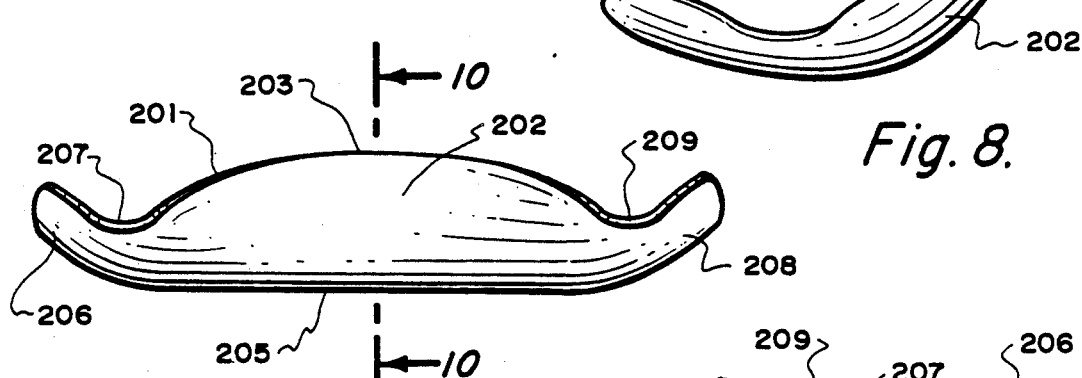
Fig. 9.
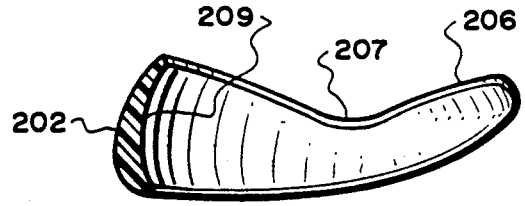
Fig. 10.

EXTENDED CHIN AND MANDIBLE IMPLANTS

This application is continuation of application Ser. No. 07/154,535, filed Feb. 16, 1988, now abandoned; which is a continuation in part of Ser. No. 06/822,172 filed 01/24/86, now abandoned.

BACKGROUND OF THE INVENTION

1. Field of the Invention

The present invention pertains to surgery; a more particularly to the orthopedics of reconstructive and aesthetic surgery including a bone prosthesis which is implantable on the chin or mandible of a patient.

2. Description of the Prior Art

The medical speciality of facial cosmetic surgery, reconstructive and plastic surgery involves reconstruction of the cutaneous tissues around the neck and face, which is performed to correct defects and to remove the marks of time.

The contour appearance of the lower jaw line has traditionally been improved by onlay implants of various designs. These are used for microgenia or underdevelopment or deficiency of the chin and jaw line either due to accident, heredity, or infection. Previous implant designs have either been of a converging concavo-convex lens (watch-glass shape), or of a solid crescent shape with bilateral tails extended around the mandible and rather square notches carved into the superior aspect in an attempt to avoid pressure upon the mental nerves. The posterior aspect of these implants has been notably flat in nature, thereby preventing its natural contour to the anterior anatomic bony configuration of the mandible.

SUMMARY OF THE INVENTION

An object of the present invention is to prevent bony erosion of the mandible, particularly in the area of the tooth roots by distributing the pressure against the irregular anterior surface of the mandible by having an implant design with a contoured posterior surface to fit the anterior surface of the mandible. Previous implant designs have not directed themselves to this problem and the issue of bone erosion has become a major concern to plastic and reconstructive surgeons throughout the world. In addition, the problem of avoiding traction or damage to the mental nerves is prohibited by this invention wherein the superior line of the implant diminishes from a full medial contour to a thinner lateral contour specifically measured to produce placement below the mental foramen and totally avoid any possibilities of traction or impingement on the mental nerves. Previous design implants with notches and lack of posterior contour to the mandible have resulted in movement and shifting of the implant in lateral directions producing impingement on nerves and incurable symptoms or intractable pain from the shifting of the notches and pressure on the mental nerves. The present implant invention avoids the problems of bone erosion and mental nerve impingement by two innovative design factors:

1(a). Contoured posterior aspect of the implant to fit the anterior surface of the mandible and distribute pressure evenly;

1(b). Posterior design further stablizes the implant in the midline and avoids lateral movement.

2. Superior contour of the implant to a tapered shape beneath the mental foramina as opposed to a discrete notch totally eliminates the possibilities of mental nerve impingement, damage and chronic or intractable symptoms.

This unique new chin implant design invention eliminates several critical factors which have made chin implants controversial to present day reconstructive surgeons.

3. It produces normal and natural jaw contour by the lateral extension of the implant.

4. It avoids damage or pressure on the mental nerves by contouring of the superior border of the implant inferior to the mental foramina as opposed to notching of the superior border around the mental foramina which can produce pressure symptoms with the slightest bit of lateral displacement.

5. The contour of the posterior aspect of the implant to the anterior mandible configuration prevents lateral displacement and thereby minimizes any problems of displacement or of mental nerve dysfunction. Such posterior implant contouring also eliminates or minimizes the possibilities of the anterior mandible bone erosion causing possible harm to the anterior lower mandibular teeth roots. There are other versions of the chip implant described in this application. Three of these other versions could be described as mandible implants, which modify and change the appearance of the entire mandible, rather that just the chin. For example, there is a third alternate embodiment of the implant which modifies the bulbous prominence of implants 2 and 50 in the medial crest and reduces that component and flattens out the height of the medial part of the implant. In this alternate embodiment, the cross section of the implant is much thicker, the height is less and the two tails taper to shorter ends. The mental foramina are avoided by having a pair of bilateral indentations on the upper edge of the implant.

A fourth alternate embodiment of the chin implant is called a chin shell implant. There is disclosed a front portion which resembles half of an elongate clam shell and attached to this frontal portion are a pair of side flanks. This implant has a fuller frontal portion compared with the first, second, and third alternative embodiments. The purpose of this large frontal portion is to provide more of a buildup for that particular patient whose receding chin requires more of a fuller buildup to create the appearance of a naturally appearing chin and mandible. Also, in this version, the cross-sectional width of the implant is less and as a result this implant is more pliable. The lower edge of the implant defines the lower border of the patient's mandible. This implant could be described as a mandible overlay.

In a fifth alternate embodiment of the chin implant, also called a chin shell, there is also shown a front portion resembling an elongate clam shell shape having a pair of bilateral side flank portions acting as side anchoring points for the implant. The side flank portions also modify the appearance of the mandible. In this version, the lower edge is thicker than in the fourth embodiment and wraps around the lower border of the mandible to further define it. Additionally, the upper edge rides much higher on the mandible. The front portion acts to cup over or overlay the whole frontal portion of the patient's mandible, also known as the mental protuberance. This inplant finds use where the patient not only has a receding chin, but also has a low rising chin, that is, little distance between the lower lip and the bottom rim of the lower jawbone or base of the chin. By means of the implantation of this chin shell, the entire lower edge of the implant redefines the mandible of the patient. This implant gives the appearance of a projecting chin is profile, and the chin area of the patient appears to be longer in the frontal perspective.

In a sixth alternate embodiment of the mandible implant, there is a version for modifying a patient who has a pointed chin, commonly described as a chisel point chin or an anvil shaped chin. In this patient, the chin area, or mentum, is not receding in that the jaw itself is prominent enough, but it is not square appearing and comes to a prominent point. This sixth alternate embodiment has a front portion and a pair of extensive bilateral flank portions to help hold this implant in position and to redefine the mandible. The portions forming the pair of side flanks merge with the front portion to create a U-shaped type of implant when viewed from the top plan view. The lower edge of this implant has a pronounced cutaway medial portion so that the medial cutaway portion of the bottom edge rests adjacent to the point of the mandible. Additionally, the front portion has a very transverse cross-section. This prominent front portion pushes out on the sides of the patient's mandible to create a more squared off lock to overcome the pointedness caused by the patient's natural pointed mandible.

BRIEF DESCRIPTION OF THE DRAWINGS

FIG. 5 is a perspective view of a third alternate embodiment of the invention.

FIG. 6 is a front elevational view of FIG. 5.

FIG. 7 is a cross-sectional view taken along the lines 7—7 of FIG. 6.

FIG. 8 illustrates a fourth alternate embodiment of the invention and is a perspective view.

FIG. 9 is a front or anterior elevational view of the implant illustrated in FIG. 8.

FIG. 10 is a cross-sectional view taken along the line 10—10 of FIG. 9.

DETAILED DESCRIPTION OF THE PREFERRED EMBODIMENT

Figure 1:
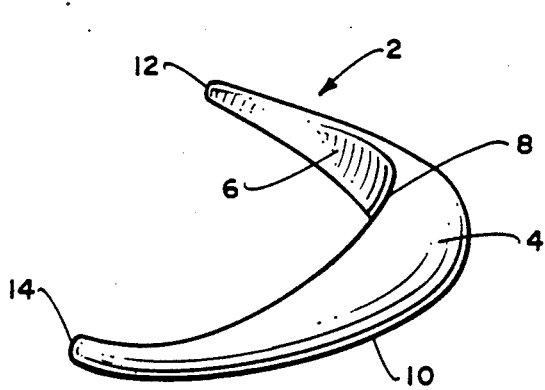
FIG. 1 is a perspective view of the chin implant.
Figure 4:
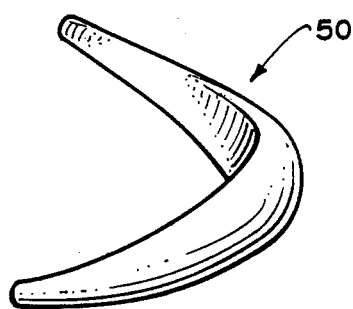
FIG. 4 is a perspective view of a smaller version of the implant shown in FIG. 1.

Referring now to the drawings, FIGS. 1 and 4 each disclose a perspective view of the extended chin implant. A preferred embodiment of the extended chin implant is labelled as 2. The implant 2 can be described a three dimensional curved implant having an anterior surface 4 and a posterior surface 6. A top plan view of the implant (not shown) would illustrate a generally crescent-shaped outline.

In medical parlance, the sagittal plane is defined as a vertical plane through the longitudinal axis of the trunk dividing the body into right and left portions which are equal and symmetrical parts. A transverse plane is a horizontal plane at right angles to the mid-sagittal plane or the vertical axis of the body.

In the context of this specification, a radial sagittal plane includes a series of vertical planes extending radially from the vertical axis and cross-secting the implant anywhere between it's bilateral ends.

The posterior surface 6 of the implant has a generally concave cross-section when sliced along any one of the imaginary radial sagittal planes. When the transplant is sliced in an imaginary transverse plane, the overall posterior surface 6 is disclosed as a concave cross section. The dual or vertical and horizontal concavity of the posterior surface allows the implant to be superposed against the bony area of the mandible or chin providing for a snug fit against the irregular surface of the mandibular region comprising the chin. This cooperation between the posterior surface 6 and the mandible will be discussed in greater detail infra.

Any cross section of the anterior surface 4 of the implant 2 formed by any one of the imaginary radial sagittal planes slicing through the implant discloses a generally convex cross-sectional view. When the implant is sliced in a transverse plane, the anterior surface includes a convex cross section. The dual or vertical and horizontal convexity of the overall anterior surface 4 provides for a naturally appearing contour to the chin area after the implant is properly implanted against the mandible of the patient. The anterior surface 4 and the posterior surface 6 merge to form a superior or upper edge 8 and an inferior or lower edge 10. The anterior and posterior surfaces also merge to form bilateral ends 12 and 14.

Figure 2:
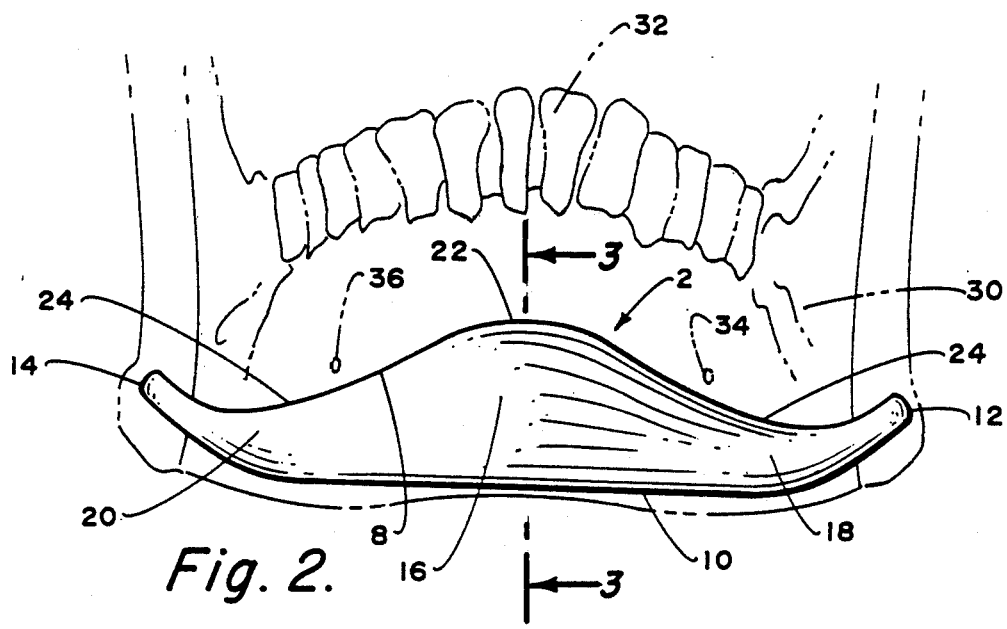
FIG. 2 is a front elevational view showing the human mandible in phantom lines with the chin implant correctly positioned on the mandible.

FIG. 2 illustrates how the implant 2 can be superposed against the mandible. There is illustrated a front elevational view of the lower jaw and lower teeth illustrated in phantom lines without the overlying soft tissues. The mandible is labelled as 30. The lower teeth are labelled as 32. On the mandible 30 are shown two openings or holes medically described as mental foramens, labelled as the left mental foramen 34 and the right mental foramen 36. These mental foramina are spaced bilaterally on the mandible 30. These foramina allow for passage of the mental nerves from behind the jaw to the outside or anterior of the jaw. The function of the mental nerves is for sensory purposes. The mental nerves are distributed in the skin and mucous membrane of the lower lip and chin.

The bilateral ends 12 and 14 of the implant are clearly illustrated in FIG. 2. Medial proturberance means on the anterior surface 4 is illustrated as a bulbous prominence, and is labelled number 16. It assists in providing a naturally appearing prominence to the medial chin area after the implant 2 is surgically implanted. The extended chin implant branches out bilaterally from the medial protuberance 16 by having two bilateral extensions 18 and 20 tapering off to their respective bilateral ends 12 and 14. The bilateral extensions also assist in lending a naturally appearing contour to the patient's chin. The superior edge 8 is well defined in FIG. 2. It flows from the crest 22 of the medial protuberance 16 tapering down on either side forming the bi-lateral extensions 18 and 20 and curving transversely and further tapering rearwardly towards the ends 12 and 14. Between the medial crest 22 of the superior edge and the bilateral ends 12 and 14, there are arcuate-shaped depression means 24 for avoiding the mental foramina. The arcuate-shaped depression means are illustrated as the bow-shaped or curved-shaped depressions on the superior aspect of the superior edge from the crest 22 down to either bilateral end 12 and 14.

This curving away 24 avoids the mental foramina 34 and 36 on either side by keeping the superior edge of the implant inferior to them. Since the overall posterior surface 6 forms a snug fit against the mandible 30, the implant 2 is precluded from shifting laterally or vertically relative to the mandible. The resulting stationary positioning of the implant prevents the implant from riding up and impinging on the mental nerves which exit through the mental foramina 34 and 36. The posterior surface also spreads and evens out the pressure exerted on the mandible caused by the soft tissue pressing against the anterior surface of the implant.

Impingement of a mental nerve can and usually does cause severe discomfort and pain to the patient. Furthermore, the fixed position of the implant will preclude the superior edge and posterior surface from rubbing against the mandible and causing bone erosion at the root line of the lower teeth 32.

Figure 3:
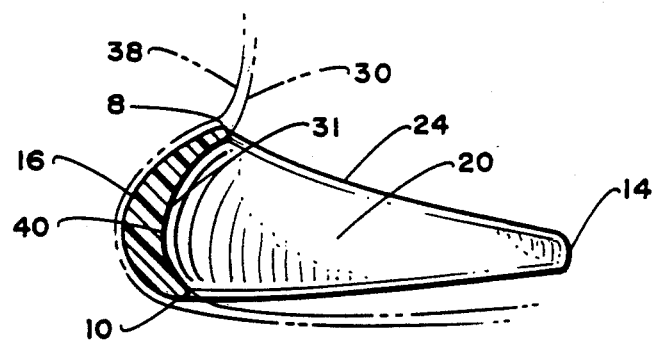
FIG. 3 is a medial sagittal cross-sectional view taken along the lines 3—3 of FIG. 2.

FIG. 3 illustrates a medial sagittal cross-sectional view of the implant taken along the line 3—3 of FIG. 2. The medial posterior proturberance 16 is well defined in this view. Also disclosed in this view is a medial concavity means on the posterior surface 6 for cooperating with the contour of the anterior surface 31 of the mandible 30. The medial concavity means is illustrated as a bilateral concave cavity 40 underlying the medial posterior proturberance 16. The concave cavity is more pronounced in the medial region, and it becomes less pronounced bilaterally as it approaches the ends 12 and 14. This changing concavity is intended to cooperate with the irregular anterior surface of the mandible in the region where the implant 2 superposes the mandible. The mandible 30 and soft tissue 38 are shown in phantom lines.

FIG. 4 illustrates a smaller version of the implant 2 shown in FIG. 1. Since the invention is intended for implantation on all sizes of patients, the smaller version 50 can be used with patients having smaller jaws. It is foreseeable that several different sizes could be fabricated to maintain an inventory which would fit the entire range of mandible sizes.

The implant 2 or 50 can be molded or otherwise fabricated using any type of biologically inert plastic such as silicone sold under the trademark Silastic by the Dow Corning Company. This type of material is pliant so that the implant can "give" when in place in response to movement of the jaw while eating, talking, swallowing or the like.

Referring now to FIGS. 5, 6 and 7, there is disclosed a third alternate embodiment of the chin implant invention. FIG. 5 shows a perspective view of the implant; FIG. 6 is a front elevational view of the implant; and FIG. 7 is a transverse cross-sectional view taken along the line 7—7 of FIG. 6.

The implant illustrated in FIGS. 5 through 7 is generally labeled as 100. The front anterior portion is 102; the inner posterior concave portion is 104 and the two bilateral tails or side portions are 106 and 108. This implant 100 has an acute medial concavity 109 on the concave portion 104 tapering out to a shallow concavity towards each of the bilateral tails 106 and 108. There is also shown a pair of dips labeled 114 and 116 which are cut away to avoid the mental foramina. This implant differs from those shown in FIGS. 1 through 4 in that the bulbous prominence labeled 118 is more pronounced and the top to bottom thickness or height of the implant is less. When placed against the mandible the implant rides lower to create a different profile after the implant is in place. This implant would be adaptable to a person with a certain type of receding chin.

FIGS. 8, 9 and 10 illustrate a fourth alternate embodiment of the chin or mandible implant invention. FIG. 8 is a perspective view of the alternate embodiment; FIG. 9 is a front elevational view of the fourth alternate embodiment; and FIG. 10 is a transverse cross-sectional view taken along the line 10—10 of FIG. 9.

The embodiment illustrated in FIGS. 8 through 10 is generally labeled as implant 200 and can be termed a chin shell. Again this implant has an anterior convex portion 202, a concave inner posterior portion 204, and a pair of bilateral tails or side portions 206, 208. The concave inner portion has a relatively acute concavity in the medial transverse section 209 flattening out to a shallower concavity towards each of the bilateral tails. The transverse cross-sectional view in FIG. 10 illustrates a different type of cross section vis-a-vis FIG. 7 in the third alternate embodiment. Likewise, this type of implant is used for patients with another type of receding chin, chin imperfection or deformity. It is up to the plastic surgeon whether or not this particular implant would be the most appropriate to create the sought after naturally appearing profile for the patient. This type of implant is used to reshape and redefine the entire mandible, not just the mentum. The bilateral portions 206 and 208 merge with the front portion 201 to form a wraparound mandible implant. The front portion has the shape of a clam shell, hence the name "chin shell" for this embodiment. The bottom edge 205 defines the lower border of the patient's mandible, the front portion and bilateral portions reshape the surface of the mandible. The upper edge 203 has cutaways 207 and 209 to avoid the mental foramina.

Figure 11:
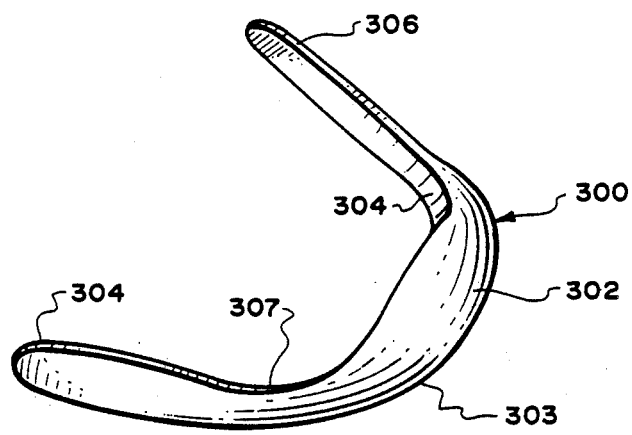
FIG. 11 is a perspective view of a fifth alternate embodiment of the invention.
Figure 12:
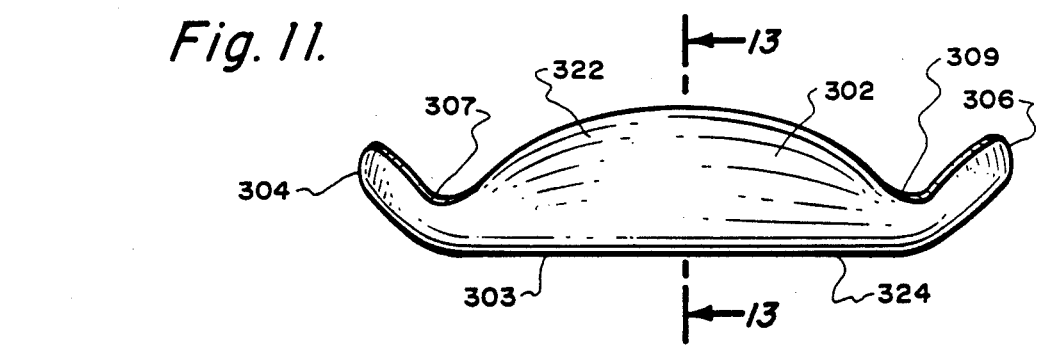
FIG. 12 is a front or anterior elevational view of the implant illustrated in FIG. 11.
Figure 13:
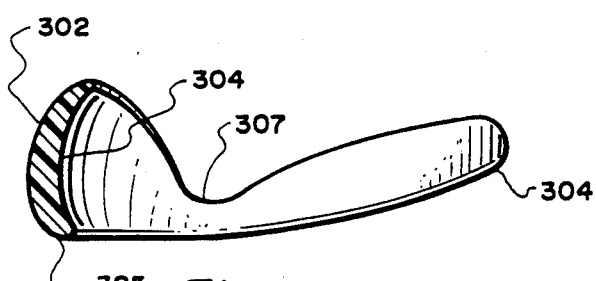
FIG. 13 is a cross-sectional view taken along the line 13—13 of FIG. 12.

FIGS. 11, 12 and 13 illustrate a fifth alternate embodiment of the chin or mandible implant invention. FIG. 11 is a perspective view of the chin implant; FIG. 12 is a front elevational view of the fifth alternate implant and FIG. 13 is a transverse cross-sectional view taken along the 13—13 of FIG. 12.

The implant described in FIGS. 11 through 13 is generally labeled as 300. Again this implant has an anterior front convex portion labeled 302 and an interior concave posterior part of the front portion labeled 304. The interior posterior portion has the concavity most pronounce at the medial portion and tending to be less pronounced as one approaches both bilateral tails. This particular implant has a high rising bulbous prominence labeled 322. As can be seen in the cross section of FIG. 13 this will tend to match up with the certain type of topography of a particular mandible. Again, this type of implant was invented to be used for a certain type of chin reshapement. In this particular case, it is intended to give greater depth to the chin for those who tend to have a short and receding chin, that is, going from the lower lip to the bottom of the chin on the patient. The inferior edge 324 tends to ride somewhat below the lower edge of the mandible creating an appearance of a longer jaw of the front view of the patient and tends to give the appearance of a mandible having more depth in the base of the chin area.

The front portion 303 merges with the bilateral side flank portions 304 and 306 to create a wraparound mandible implant. The front portion 303 is shaped like a clam shell hence the name "chin shell" for this type of implant. The lower edge 324 is thicker at 325 and wraps around the lower border of the patient's mandible. The implant can redefine the patient's entire mandible region, rather than just the mentum area of the chin. There are a pair of dips 307 and 309 to avoid the mental foramina.

Figure 14:
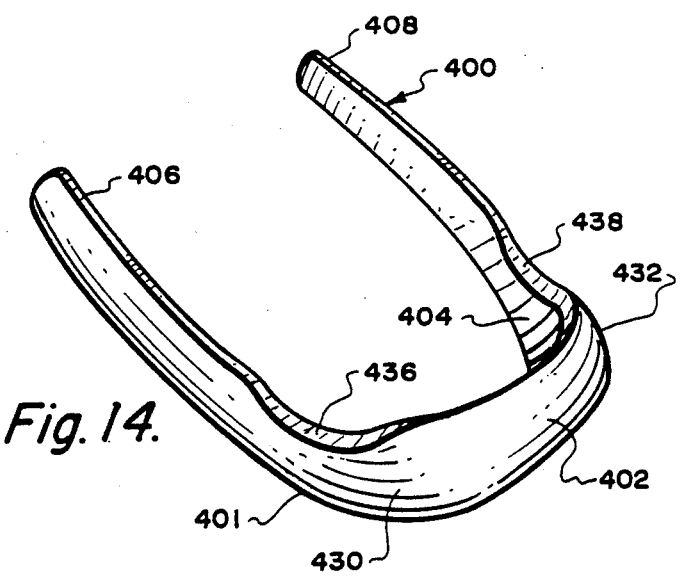
FIG. 14 illustrates a sixth alternate embodiment of the invention shown in perspective.
Figure 15:
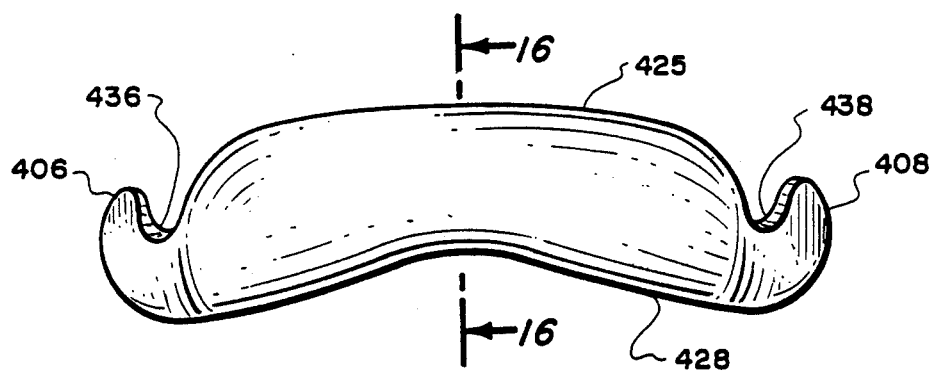
FIG. 15 is a front or anterior elevational view of the implant illustrated in FIG. 14.
Figure 16:
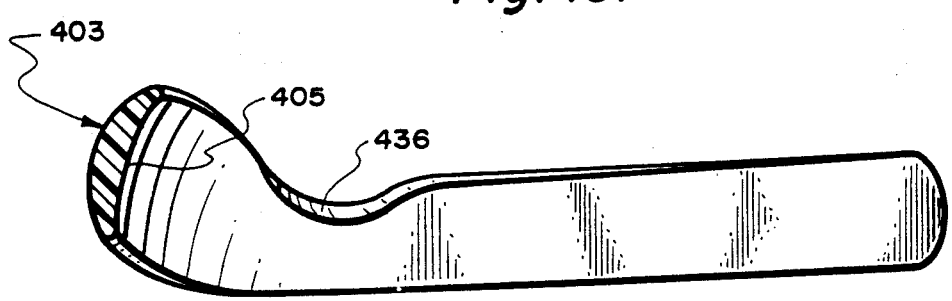
FIG. 16 is a cross-sectional view of the implant illustrated in FIG. 14 and FIG. 15 and taken along the line 16—16 of FIG. 15.
Figure 17:
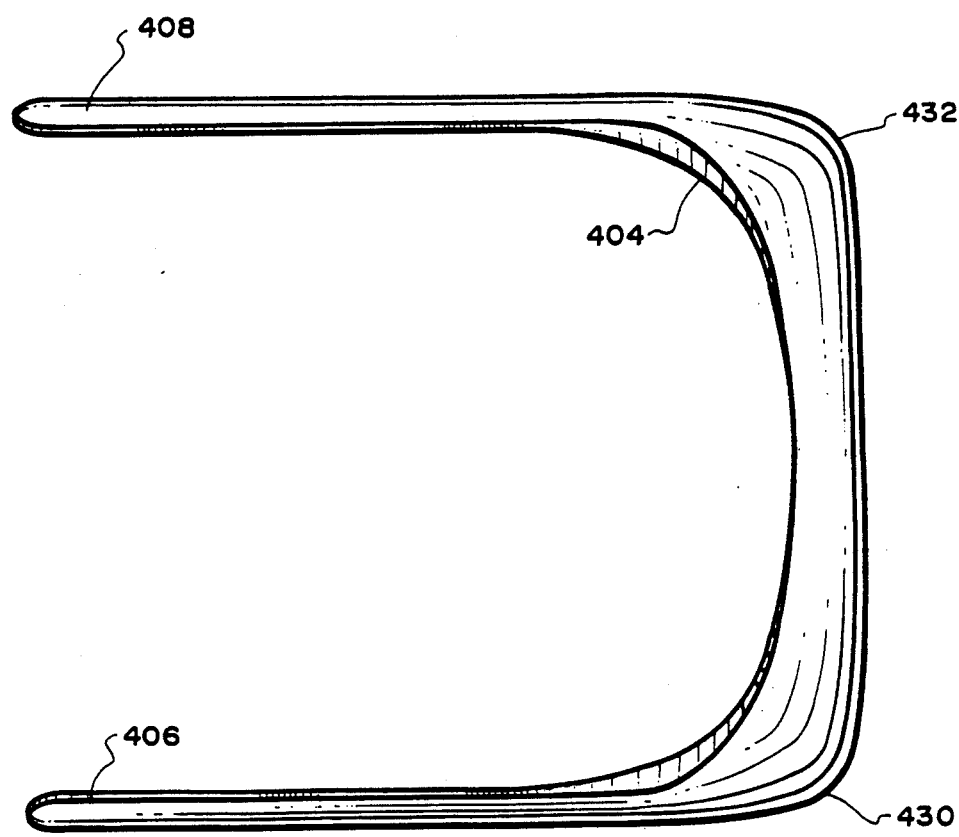
FIG. 17 is a top plan view illustrating the sixth alternate embodiment which is shown in perspective in FIG. 14.

FIGS. 14 through 17 illustrate a sixth alternate embodiment of the chin implant invention. FIG. 14 is a perspective view of the sixth alternate embodiment; FIG. 15 is a front elevational view; FIG. 16 is a transverse medial cross-sectional view taken along the line 16—16 of FIG. 15; FIG. 17 is a top plan view of the invention.

The sixth alternate embodiment of FIGS. 14 through 17 is generally labeled as 400. The outer convex anterior part of the front portion is labeled as 402. The left side flank or side portion is 406 and the right side flank or side portion is 408. The interior concave posterior portion is generally labeled as 404. The purpose of this type of implant is to square away and make more prominent the mandibular defect which can be described as a chisel point chin or an anvil type of jaw. The front portion includes an upward curved edge 425. The lower edge 428 of the front portion is placed adjacent to the anvil type of chin. The rest of the implant as shown in FIG. 17 illustrates a squaring off of the front area or the outer anterior part of the front portion of the implant generally labeled as 401. The left side flank 406 merges with the left edge of the portion 402 forming a left corner 430. The right side flank 408 merges with the other end of the front portion forming another corner 432 of the implant. There are pronounced bilateral dips of either side of the implant generally labeled as 436 and 438 which are cutaway to avoid the mental foramina.

The front elevational view of the implant shown in FIG. 15 is intended to be superimposed against the pointed chin of a typical patient. The patient's profile of the chin and lip area is omitted from these Figures. However, it is intended, as with all of the other implants described herein, that the upper edge 425 of this chin implant will be positioned somewhere below the lower lip of the patient. The lower edge 428 of the implant will be positioned to be resting at the most prominent point of the chisel type chin. The arcuate cutaway on this lower edge 428 is there so that the pointed end of the chin will meet at the medial portion of the lower edge 428. The arcuate depressions slope downwardly and merge with the side flanks 406 and 408 to create a more defined square jaw look to overcome the pointed chin appearance. Furthermore, the upper edge 425 rides much higher on the mandible and is much fuller along the outer convex anterior part of the front portion 402. This is necessary to provide bulk and add body to the pointed chin so that net result after the chin implantation is an appearance of a square shaped full sided chin on the sides of the patient in addition to a full square shaped appearance of the chin from the front. This eliminates the pointed chin appearance. The pair of side flanks 406 and 408 taper out into thin flanks and are intended to reshape and provide anchoring points on the side areas of the mandible to minimize the drifting of the implant after it has been positioned on the patient. The medial cross section of the outer convex anterior front portion is labeled 403 and illustrates the general vertical convex cross section of the front portion 402. The medial cross section of the interior concave posterior portions labeled 405 of the interior of 404 also generally indicates a transverse curved area but not as prominent a concave curve at the convex curve shown in FIG. 403.

It is foreseeable that several different sizes could be fabricated to maintain an inventory which would fit the entire range of mandible sizes.

The implants 100, 200, 300 and 400 can be molded or otherwise fabricated using any type of biologically inert plastic such as silicone sold under the trademark Silastic by the Dow Corning Company. This type of material is pliant so that the implant can "give" when in place in response to movement of the jaw while eating, talking, swallowing or the like.

Obviously, many modifications and variations of the present invention are possible in light of the above teachings. It is therefore to be understood that the full scope of the invention is not limited to the details disclosed herein, but may be practiced otherwise than as specifically described.

What is claimed is:

1. A chin shell implant used in cosmetic and reconstructive surgery for surgical incision adjacent the human mandible and underneath the fleshy portion of the chin for creating a fuller chin profile in a patient having a receding or minimal chin area comprising:
   a chin implant having a front portion;
   a left side flank portion, and an opposite right side flank portion each extending rearwardly from said front portion;
   said front portion having a front convex surface and a back concave surface, said front portion having the appearance of an elongate clam shell;
   the horizontal cross section of said front convex surface of said front portion being a convex contour;
   the vertical cross sections of said front convex surface of said front portion being variable convex contours;
   said front convex surface of said front portion having an area of greatest prominence at the lower mid-region of said front convex surface for forming a naturally appearing and aesthetically pleasing chin;
   the horizontal cross section of said back surface of said front portion having a concave contour for close positioning of the implant against the mandible;
   the vertical cross sections of said back concave surface having variable concave contours;
   said back concave surface having an area of acute concavity behind said lower mid-region of said front convex surface for providing a snug fit against the underlying mandible;
   said vertical concave cross sections having the most acute concave contour at said area of acute concavity, said vertical contours becoming less acute on either side of said area of said acute concavity and flattening out when going to the ends of both said flank portions;
   said front portion forming a lower edge which is relatively flat and is for being positioned below the lower rim if a patient's mandible after the implant is surgically implanted for giving the appearance of a fuller chin on the patient by pushing out the overlying fleshy portion of the patient's chin;

said front portion, said left side flank portion, and said right side flank portion forming an upper edge on said implant;

said upper edge having an arcuate medial area for riding high upon the chin area of said patient for creating a fuller chin and mandible appearance;

said medial upward portion of said upper edge tapering downward toward said flank portions and further including a pair of bilateral cutaways on said upper edge for avoiding the mental foramina.

2. The implant as recited in claim 1 wherein said lower edges includes an inferior extension which descends into the soft tissue of the chin and causes the body to react to said implant by encapsulating said inferior extension by forming a type of collagen fibrosis which will not stick to said implant, but will snugly hold said inferior extension in place by forming a pocket to keep said implant from drifting.

3. A chin shell implant for creating a fuller chin profile in a patient suffering from a receding or minimal chin area comprising:

a chin implant having a front portion;

a left side tail portion and an opposite right side tail portion each extending rearwardly and angled slightly upwardly from said front portion;

said front portion having an anterior convex surface and a posterior concave surface;

said front portion having a lower edge for giving the appearance of a fuller chin on the recipient;

said front portion, said left side tail portion, and said right side tail portion forming an upper edge and a lower edge on said implant;

said upper edge having an arcuate medial area for rising high on the chin area of a recipient for creating a fuller chin and mandible appearance;

said medial upward arcuate portion of said upper edge tapering downward toward both said side tail portions and further including a pair of bilateral dips on said upper edge for avoiding the mental foramina;

said lower edge being curvilinear.

4. A chin implant used in cosmetic and reconstructive surgery for surgical incision adjacent the mental protuberance of the human mandible and the fleshy portion of the chin area which comprises:

a three-dimensional implant having an outer generally convex surface having a lower mid-region, and an inner concave surface;

said outer convex surface in said lower mid-region thereof, having a convex surface both in a longitudinal and transverse cross section such that at an intersection of the surfaces forms a maximum apex to yield an area of greatest prominence for forming a naturally appearing chin when implanted for aesthetic purposes;

said outer convex surface and said inner concave surface merging to form an upper edge, a lower edge, and a pair of opposite transversely positioned bilateral tails extending rearwardly;

said upper edge having a medial riser portion, and a pair of bilateral cutaways for avoiding the mental nerves; and said oppositely positioned bilateral tails being inclined upwardly relative to the main body of said implant as they extend rearwardly.

* * * * *